US009314642B2

(12) United States Patent
Ozawa et al.

(10) Patent No.: US 9,314,642 B2
(45) Date of Patent: Apr. 19, 2016

(54) CLOSED LOOP CHARGER FOR AN IMPLANTABLE MEDICAL DEVICE SYSTEM EMPLOYING REFLECTED IMPEDANCE MODULATION

(75) Inventors: Robert Ozawa, Woodland Hills, CA (US); Daniel Aghassian, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 252 days.

(21) Appl. No.: 13/608,666

(22) Filed: Sep. 10, 2012

(65) Prior Publication Data

US 2013/0096652 A1 Apr. 18, 2013

Related U.S. Application Data

(60) Provisional application No. 61/546,871, filed on Oct. 13, 2011.

(51) Int. Cl.
*A61N 1/37* (2006.01)
*A61N 1/378* (2006.01)
*A61N 1/372* (2006.01)

(52) U.S. Cl.
CPC ........... *A61N 1/3787* (2013.01); *A61N 1/37252* (2013.01)

(58) Field of Classification Search
CPC ............................... A61N 1/3981; A61N 2/02
USPC ..................................................... 607/61, 62
See application file for complete search history.

(56) References Cited

U.S. PATENT DOCUMENTS

| | | | |
|---|---|---|---|
| 3,942,535 A | 3/1976 | Schulman | |
| 6,516,227 B1 | 2/2003 | Meadows et al. | |
| 6,553,263 B1 * | 4/2003 | Meadows | A61N 1/36071 607/33 |
| 2004/0267501 A1 * | 12/2004 | Freed | H02J 7/025 702/184 |
| 2005/0085873 A1 * | 4/2005 | Gord et al. | 607/61 |

(Continued)

FOREIGN PATENT DOCUMENTS

| | | |
|---|---|---|
| JP | 2003-348774 A | 12/2003 |
| WO | 2009/051537 A1 | 4/2009 |

OTHER PUBLICATIONS

U.S. Appl. No. 61/414,616, filed Nov. 17, 2010, Carbunaru, et al.

(Continued)

*Primary Examiner* — Theodore Stigell
*Assistant Examiner* — Natasha Patel
(74) *Attorney, Agent, or Firm* — Lewis, Reese & Nesmith, PLLC

(57) ABSTRACT

The disclosed system for providing closed loop charging between an external charger and an implantable medical device such as an IPG involves the use of reflected impedance modulation, i.e., by measuring at the external charger reflections arising from modulating the impedance of the charging coil in the IPG. During charging, the charging coil in the IPG is periodically pulsed to modulate its impedance. The magnitude of the change in the coil voltage produced at the external charger $\Delta V$ as a result of these pulses is assessed and is used by the controller circuitry in the external charger as indicative of the coupling between the external charger and the IPG. The external charger adjusts its output power (e.g., Icharge) in accordance with the magnitude of $\Delta V$, thus achieving closed loop charging without the need of telemetering coupling parameters from the IPG.

13 Claims, 8 Drawing Sheets

(56) References Cited

U.S. PATENT DOCUMENTS

2006/0187607 A1* 8/2006 Mo .............................. 361/143
2009/0118796 A1 5/2009 Chen et al.
2010/0137948 A1 6/2010 Aghassian et al.
2010/0204756 A1 8/2010 Aghassian
2011/0004278 A1 1/2011 Aghassian et al.
2011/0046699 A1 2/2011 Mazanec
2011/0087307 A1 4/2011 Carbunaru et al.
2011/0093048 A1 4/2011 Aghassian et al.
2011/0112610 A1 5/2011 Rahman et al.
2011/0112611 A1 5/2011 Aghassian
2011/0121777 A1 5/2011 Carbunaru et al.
2011/0196452 A1* 8/2011 Forsell ............................ 607/60
2011/0276111 A1 11/2011 Carbunaru et al.
2012/0119699 A1 5/2012 Carbunaru et al.
2014/0074186 A1* 3/2014 Faltys et al. ..................... 607/61

OTHER PUBLICATIONS

U.S. Appl. No. 61/546,850, filed Oct. 13, 2011, Ozawa.
International Search Report regarding application No. PCT/US2012/057593 dated Dec. 13, 2012.

* cited by examiner

100
LSK data
= [01010]
Vbat
Ibat
26
charging/
protection
134
rectifier
132
LSK module
155
μC
140
99
18
142
141
25
power
LSK
data
50
17
Icharge
charge
122
Vcoil
+
−
ΔV
>
Vt1
demod
123
LSK
data
μC
144
alignment
indicator 162
'0'
'1'
'0'
'1'
'0'
ΔV
Vcoil1
Vcoil0

CLOSED LOOP CHARGER FOR AN IMPLANTABLE MEDICAL DEVICE SYSTEM EMPLOYING REFLECTED IMPEDANCE MODULATION

CROSS REFERENCE TO RELATED APPLICATIONS

This is a non-provisional filing of U.S. Provisional Patent Application Ser. No. 61/546,871, filed Oct. 13, 2011, which is incorporated by reference, and to which priority is claimed.

This application is related to a U.S. Provisional Patent Application Ser. No. 61/546,850, filed Oct. 13, 2011.

FIELD OF THE INVENTION

The present invention relates to wireless external chargers for use in implantable medical device systems.

BACKGROUND

Implantable stimulation devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The description that follows will generally focus on the use of the invention within a Spinal Cord Stimulation (SCS) system, such as that disclosed in U.S. Pat. No. 6,516,227. However, the present invention may find applicability in any implantable medical device system.

As shown in FIGS. 1A-1C, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 is coupled to electrodes 106 via one or more electrode leads (two such leads 102 and 104 are shown), such that the electrodes 106 form an electrode array 110. The electrodes 106 are carried on a flexible body 108, which also houses the individual signal wires 112 and 114 coupled to each electrode. In the illustrated embodiment, there are eight electrodes on lead 102, labeled $E_1$-$E_8$, and eight electrodes on lead 104, labeled $E_9$-$E_{16}$, although the number of leads and electrodes is application specific and therefore can vary. The leads 102, 104 couple to the IPG 100 using lead connectors 38*a* and 38*b*, which are fixed in a non-conductive header material 36, which can comprise an epoxy for example.

As shown in the cross-section of FIG. 1C, the IPG 100 typically includes an electronic substrate assembly including a printed circuit board (PCB) 16, along with various electronic components 20 mounted to the PCB 16, some of which are discussed subsequently. Two coils (more generally, antennas) are generally present in the IPG 100: a telemetry coil 13 used to transmit/receive data to/from an external controller (not shown); and a charging coil 18 for charging or recharging the IPG's battery 26 using an external charger 50 (discussed further below). In this example, the telemetry coil 13 and charging coil 18 are within the case 30, as disclosed in U.S. Patent Publication 2011/0112610. (FIG. 1B shows the IPG 100 with the case 30 removed to ease the viewing of the two coils 13 and 18). However, the telemetry coil 13 may also be mounted within the header 36 of the IPG 100 (not shown).

FIG. 2 shows the IPG 100 in communication with external charger 50 just mentioned. The external charger 50 is used to wirelessly convey power to the IPG 100, which power can be used to recharge the IPG's battery 26. The transfer of power from the external charger 50 is enabled by a coil (antenna) 17. The external charger 50, like the IPG 100, also contains a PCB 70 on which electronic components 72 are placed. Again, some of these electronic components 72 are discussed subsequently. A user interface 74, including touchable buttons and perhaps a display and a speaker, allows a patient or clinician to operate the external charger 50. A battery 76 provides power for the external charger 50, which battery 76 may itself be rechargeable. The external charger 50 can also receive AC power from a wall plug. A hand-holdable case 77 sized to fit a user's hand contains all of the components.

Power transmission from the external charger 50 to the IPG 100 occurs wirelessly, and transcutaneously through a patient's tissue 25, via inductive coupling. FIG. 3 shows details of the circuitry used to implement such functionality. Coil 17 in the external charger 50 is energized via charging circuit 122 with a constant non-data-modulated AC current, Icharge, to create an AC magnetic charging field. This magnetic field induces a current in the charging coil 18 within the IPG 100, which current is rectified (132) to DC levels, and used to recharge the battery 26, perhaps via a charging and battery protection circuit 134 as shown. The frequency of the magnetic charging field can be perhaps 80 kHz or so. When charging the battery 26 in this manner, is it typical that the case 77 of the external charger 50 touches the patient's tissue 25, although this is not strictly necessary.

The IPG 100 can also communicate data back to the external charger 50 during charging using reflected impedance modulation, which is sometimes known in the art as Load Shift Keying (LSK). Such back telemetry from the IPG 100 can provide useful data concerning charging to the external charger 50, such as the capacity of the battery 26, or whether charging is complete and the external charger 50 can cease.

Control circuitry 140 in the IPG 100 monitors the battery voltage, Vbat, and with the assistance of LSK module 155, produces LSK data. The control circuitry 140 can include a microcontroller for example, and may be associated with Analog-to-Digital (A/D) conversion circuitry to process and interpret the battery voltage. LSK module 155 preferably operates as software in the control circuitry 140, and assesses the incoming battery voltage to produce appropriate LSK data at appropriate times. Such LSK data is sent as a serial string of bits along line 99 to the gates of load transistors 141 and 142. The LSK data modulates the state of transistors 141 and 142, which in turn modulates the impedance of the coil 18. When LSK data=1, the transistors 141 and 142 are on (shorted) which shorts each end of the coil 18 to ground. When LSK data=0, the transistors are off (opened). The impedance of the coil 18 may also be modulated by a single transistor in series with the coil 18, which modulates the impedance by opening the coil, as shown in dotted lines.

Such modulation of the charging coil 18 is detectable at the external charger 50. Due to the mutual inductance between the coils 17 and 18, any change in the impedance of coil 18 affects the voltage needed at coil 17, Vcoil, to drive the charging current, Icharge: if coil 18 is shorted (LSK data=1), Vcoil increases to maintain Icharge; if not shorted (LSK data=0), Vcoil decreases. In this sense, the impedance modulation of coil 18 is "reflected" back to the transmitting coil 17, and thus data can be said to be "transmitted" from the IPG 100 to the external charger 50, even if not transmitted in the traditional sense. An example Vcoil waveform arising from transmission of an example sequence (LSK data=01010) is shown at the bottom of FIG. 3, and shows the data states as modulated by the ~80 kHz frequency of the magnetic field.

The Vcoil waveform is processed at demodulation circuitry 123 to recover the transmitted LSK data. To be reliably detected, the difference in coil voltage (ΔV) between the transmitted '0' ($Vcoil_0$) and '1' ($Vcoil_1$) states must as a practical matter be greater than a threshold voltage inherent in the demodulator 123, Vt1. Depending on the particularly of the circuitry, Vt1 can be rather small, ranging from 50 mV to 100 mV for instance, and can be statistically determined based on suitable bit error rates for LSK transmission.

The serial stream of demodulated bits is then received at control circuitry 144 operating in the external charger 50, so that appropriate action can be taken. The control circuitry 144 can again include a microcontroller for example. For example, if an alternating stream of bits is received (01010101 . . . ), this might be interpreted by the control circuitry 144 that the battery 26 in the IPG 100 is full, and therefore that charging can cease. In such an instance, the control circuitry 144 can suspend the production of the magnetic charging field (i.e., setting Icharge to 0), and may notify the user of that fact (by a graphical display, an audible beep, or other indicator).

Because LSK telemetry works on a principle of reflection, LSK data can only be communicated from the IPG 100 to the external charger 50 during periods when the external charger is active and is producing a magnetic charging field.

An issue arising when inductive coupling is used for power transmission relates to the coupling between the coils 17 and 18 in external charger 50 and the IPG 100. Coupling, generally speaking, comprises the extent to which power expended at the transmitting coil 17 in the external charger 50 is received at the coil 18 in the IPG 100. It is generally desired that the coupling between coils 17 and 18 be as high as possible: higher coupling results in faster charging of the IPG battery 26 with the least expenditure of power in the external charger 50. Poor coupling is disfavored, as this will require high power drain (i.e., a high Icharge) in the external charger 50 to adequately charge the IPG battery 26. The use of high power depletes the batteries 76 (if any) in the external charger 50, and more importantly can cause the external charger 50 to heat up, and possibly burn or injure the patient.

Coupling depends on many variables, such as the permeability of the materials used in the external charger 50 and the IPG 100, as well materials inherent in the environment. Coupling is also affected by the relative positions of the external charger 50 and IPG 100, as shown in FIGS. 4A-4D. For best coupling, it is preferred that axes around which coils 17 and 18 are wound (17' and 18') are parallel and collinear, and that the coils 17 and 18 as close as possible (d1) to each other, as shown in FIG. 4A. Distance d1 indicates the depth between the external charger 50 and the IPG 100, and is generally constant given that the external charger is generally placed on the patient's tissue 25, and that the IPG 100 has been implanted at a particular depth. Deviations from these ideal conditions will generally reduce coupling, as shown in FIGS. 4B-4D. In FIG. 4B for instance, the coil axes 17' and 18' are not collinear, but instead are laterally offset (x). In FIG. 4C, the coil axes 17' and 18' are not parallel, but instead have an angle θ between them. In FIG. 4D, the coil axes 17' and 18 are parallel and collinear, but the IPG 100 is relatively deep (d2).

In any of these non-ideal cases 4B-4D, coupling will be reduced, meaning that the external charger 50 must output more power (e.g., Icharge must be higher) to affect the same charging rate of the IPG's battery 26. In a closed loop charging system, the relative degree of coupling between the external charger 50 and the IPG 100 is assessed, and is used to change the output power accordingly. Prior systems have quantified this coupling in different ways. In one approach, data indicative of the coupling is read at the IPG 100 and telemetered back to the external charger 50, which again can adjust its output power accordingly. See U.S. Patent Publication 2011/0087307. But this approach adds additional complexity to the system. Applicants have found a new way of quantifying coupling in the external charger/IPG system that doesn't rely on telemetry of coupling parameters from the IPG, which is easy to implement, and which therefore results in an improved closed loop charging system.

DETAILED DESCRIPTION

The description that follows relates to use of the invention within a spinal cord stimulation (SCS) system. However, it is to be understood that the invention is not so limited, and could be used with any type of implantable medical device system.

The disclosed system for providing closed loop charging between an external charger and an implantable medical device such as an IPG involves the use of reflected impedance modulation, i.e., by measuring at the external charger reflections arising from modulating the impedance of the charging coil in the IPG. Reflected impedance modulation has been used in legacy systems to enable Load Shift keying (LSK) telemetry to send data to the external charger to control charging, as discussed in the Background. However, the technique of this disclosure doesn't involve data transmission, although some of the same LSK hardware can be used. During charging, the charging coil in the IPG is periodically pulsed to modulate its impedance. The magnitude of the change in the coil voltage (ΔV) produced at the external charger as a result of these pulses is assessed and is used by the controller circuitry in the external charger as indicative of the coupling between the external charger and the IPG. The external charger adjusts its output power (e.g., Icharge) in accordance with the magnitude of ΔV, thus achieving closed loop charging without the need of telemetering coupling parameters from the IPG.

Figure 1A:
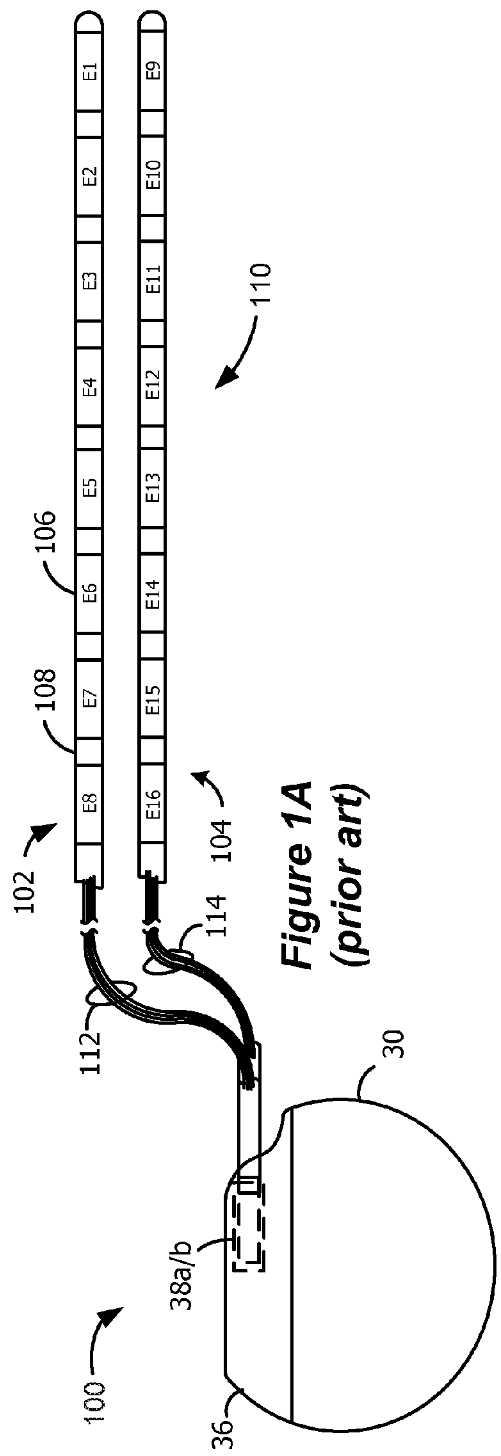
FIGS. 1A-1C show different views of an implantable medical device, specifically an Implantable Pulse Generator (IPG).
Figure 1B:
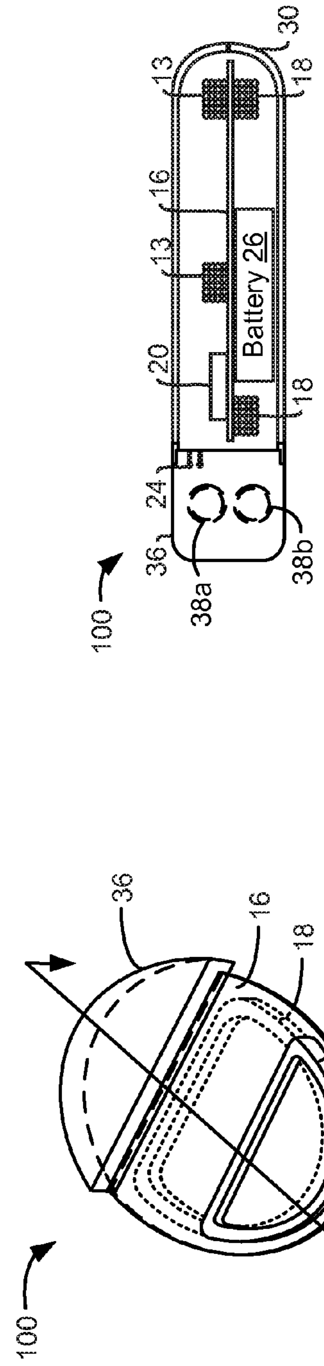
Figure 1C:
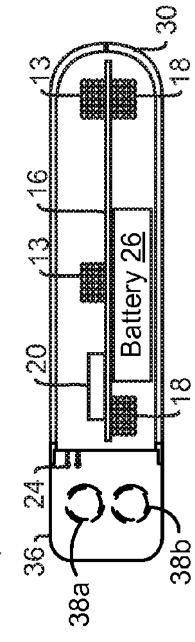
Figure 2:
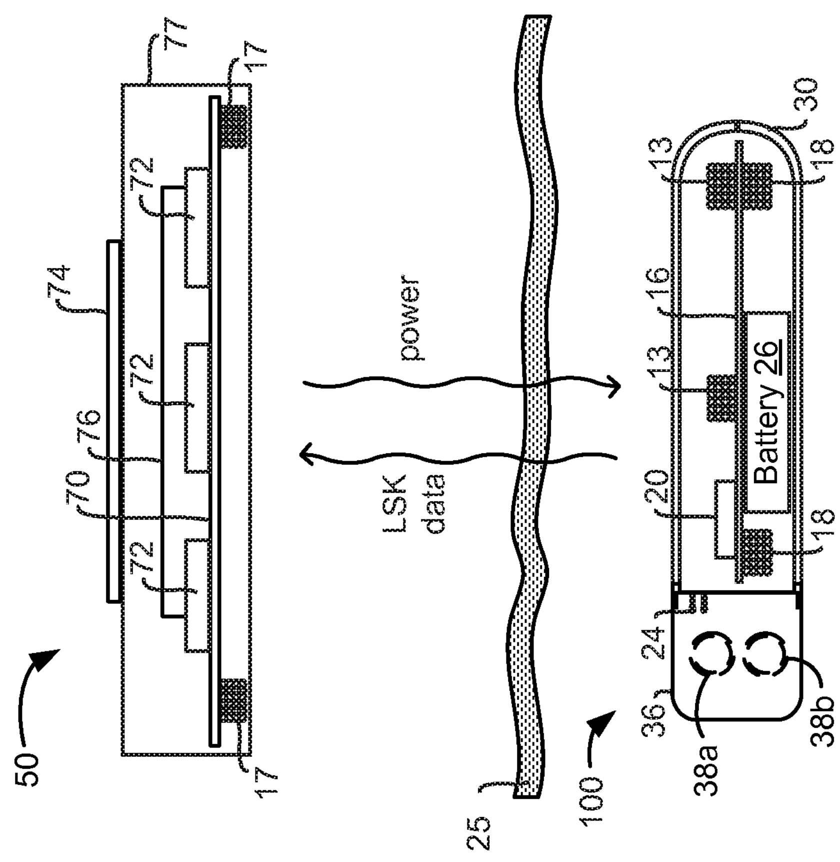
FIG. 2 shows wireless links between the IPG and an external charger.
Figure 3:
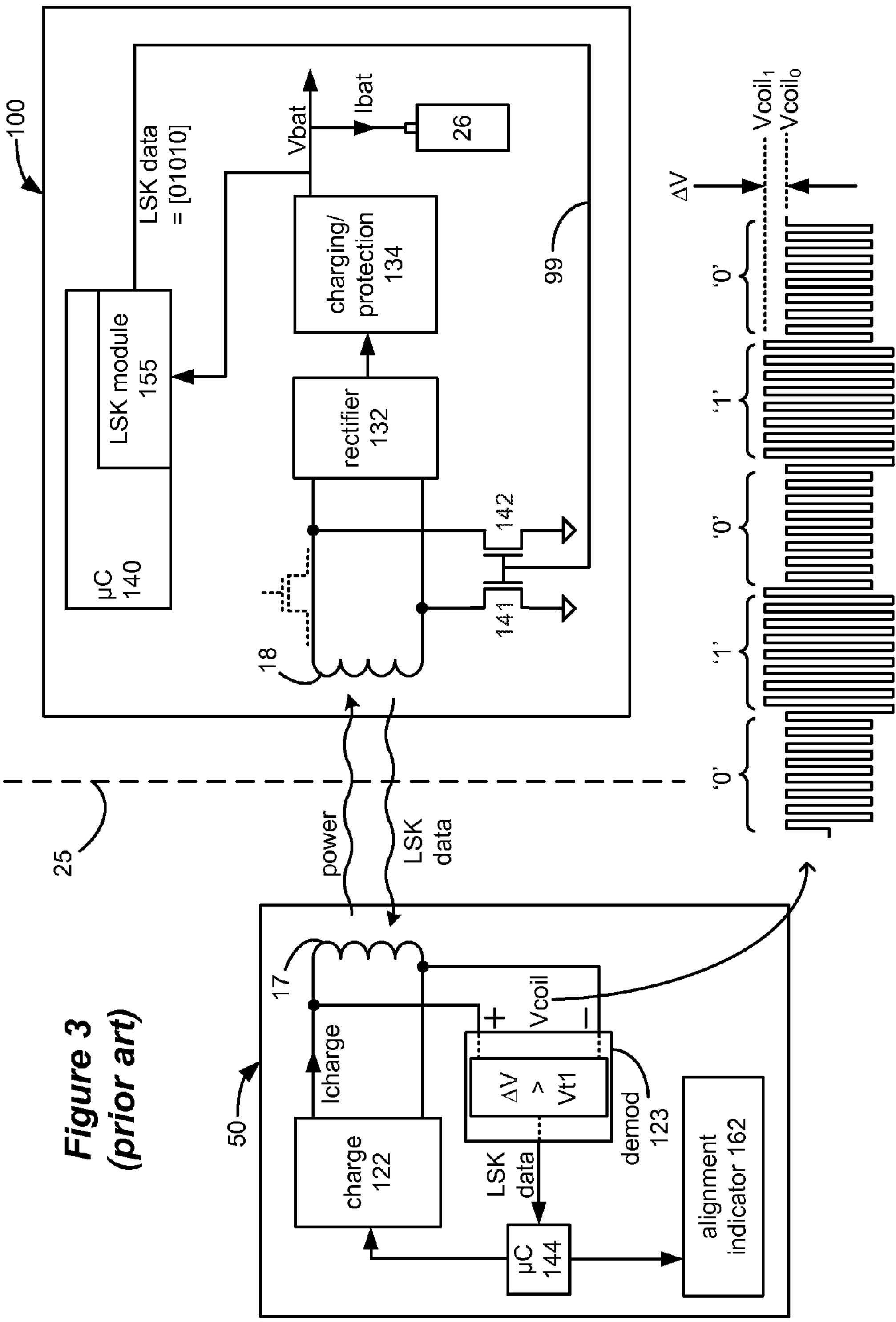
FIG. 3 shows circuitry in both the IPG and external charger for providing power to the IPG, and for telemetering data to the external charger using reflective impedance modulation to control charging.
Figure 4A:
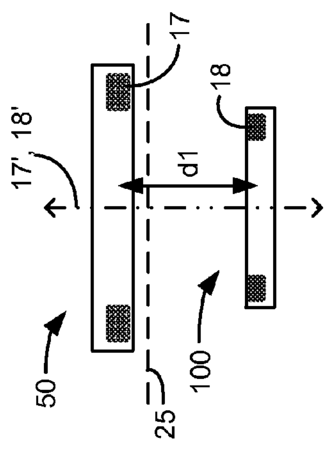
FIG. 4 shows alignment and coupling between the IPG and external charger for various orientations.
Figure 4B:
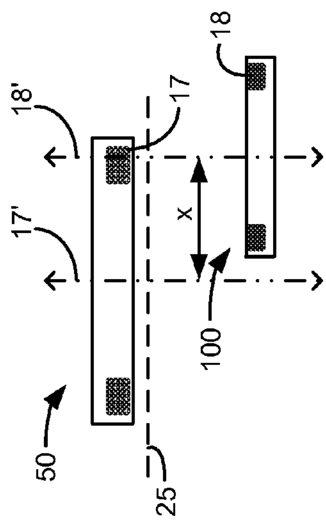
Figure 4C:
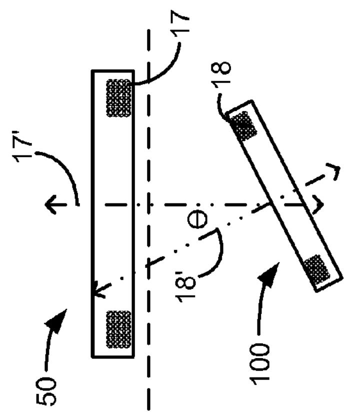
Figure 4D:
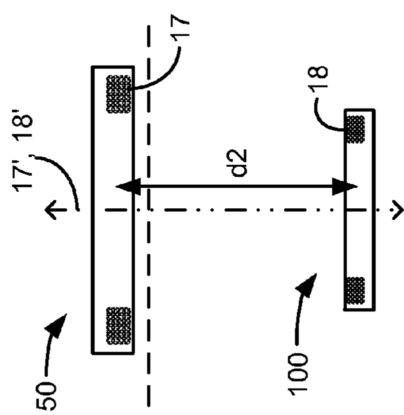
Figure 5:
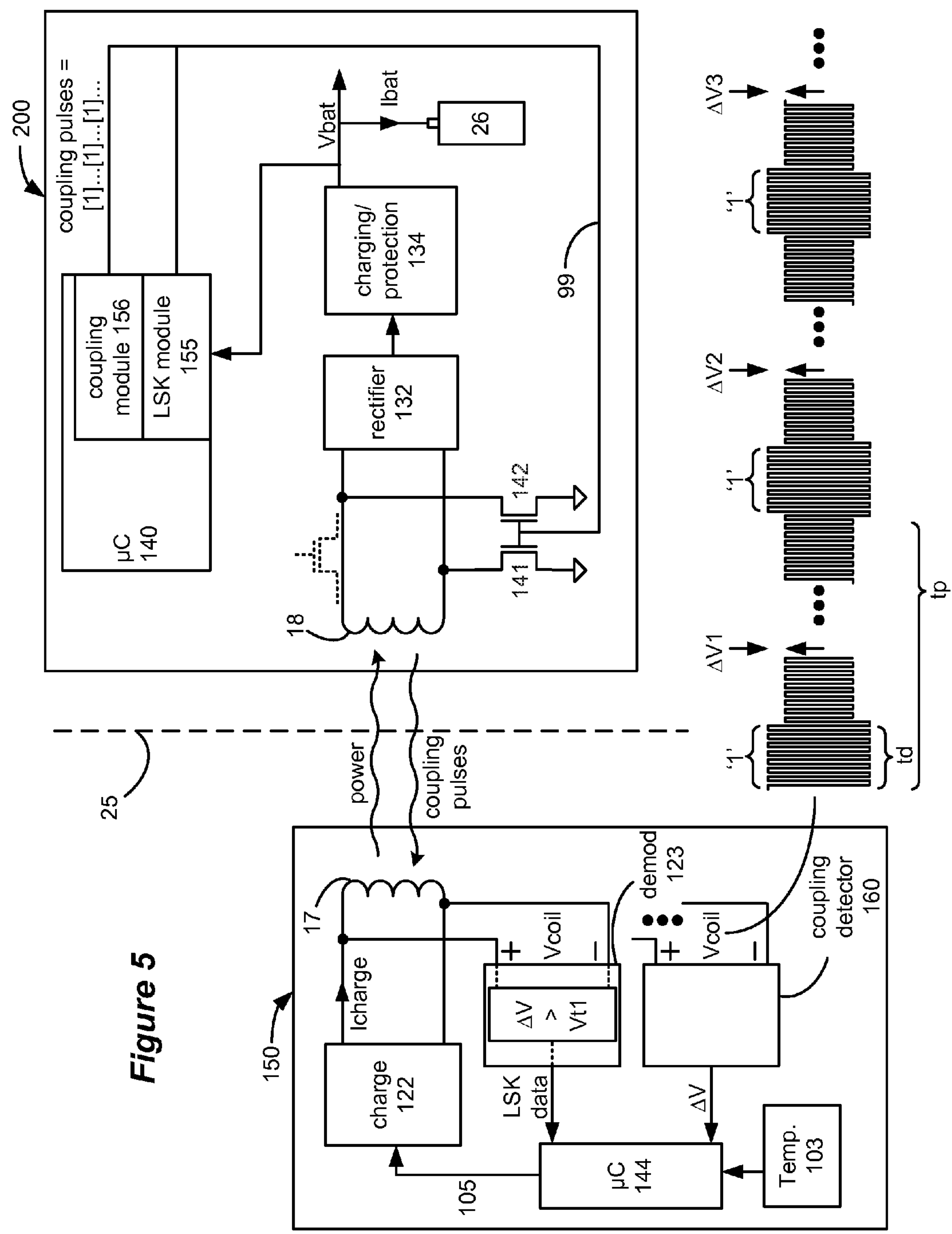
FIG. 5 shows circuitry for an improved IPG/external charger system in which reflected impedance modulation is used to provide coupling information, and in particular the use of a difference in the coil voltage (ΔV) as indicative of coupling.

An improved external charger 150/IPG 200 system having such functionality is shown schematically in FIG. 5. Starting with the IPG 200, the basic hardware remains unchanged form the IPG 100 discussed earlier. As before, an LSK module 155 monitors the voltage of the battery 26 (Vbat) during charging, and when necessary telemeters LSK data back to the external charger, starting with the issuance of serial data bits on line 99. New to IPG 200 however is a coupling module 156, which like LSK module 155 also preferably operates as software in the control circuitry 140. During reception of a magnetic charging field, the coupling module 156 periodically issues coupling pulses on line 99 to modulate the impedance of the transistors 141 and 142. As shown, these coupling pulses can comprise the periodic issuance of a logic '1' pulse (which shorts the charging coil 18 to ground) followed by an extended period of no pulse (i.e., line 99 is set to '0').

The timing of the coupling pulses can vary, but in one example the coupling pulses have a duration (td) of 2 ms and a period (tp) of 200 ms. Notice that this relationship between td and tp means that the charging coil 18 is only shorted—and hence unable to receive to power for battery recharging—for 1% of the time, which does not significantly extend the time needed to recharge the battery 26. Both of these timing parameters can be modified over the course of a charging session.

Unlike LSK data, the coupling pulses issued by the coupling module 156 are not data per se. They are only meant to occasionally modulate the impedance of the charging coil 18 for the purpose of creating reflections assessable at the external charger 150 to infer the coupling between the external charger 150 and the IPG 200. It is preferred that the coupling pulses be obviously different from the expected structure of LSK data so that they are not misinterpreted at the external charger 150. For example, if normal LSK data to suspend charging comprises alternating logic states (01010 . . . ) as discussed in the Background, then a single coupling pulse followed by a long absence of pulses (effectively, 1000000000 . . . ) is not likely to be misinterpreted at the demodulator 123 as data for controlling the external charger 150.

The reflections produced in Vcoil at the external charger 150 by the coupling pulses are shown in FIG. 5. In this example, Vcoil can as before be assessed at demodulator 123 to decode LSK telemetry, and to control charging accordingly. However, Vcoil is additionally assessed in this embodiment at separate coupling detection circuitry 160. The coupling detection circuitry 160 assesses the magnitude of ΔV, i.e., the difference in voltage between reflected '1' and '0' coupling pulses.

Figure 6:
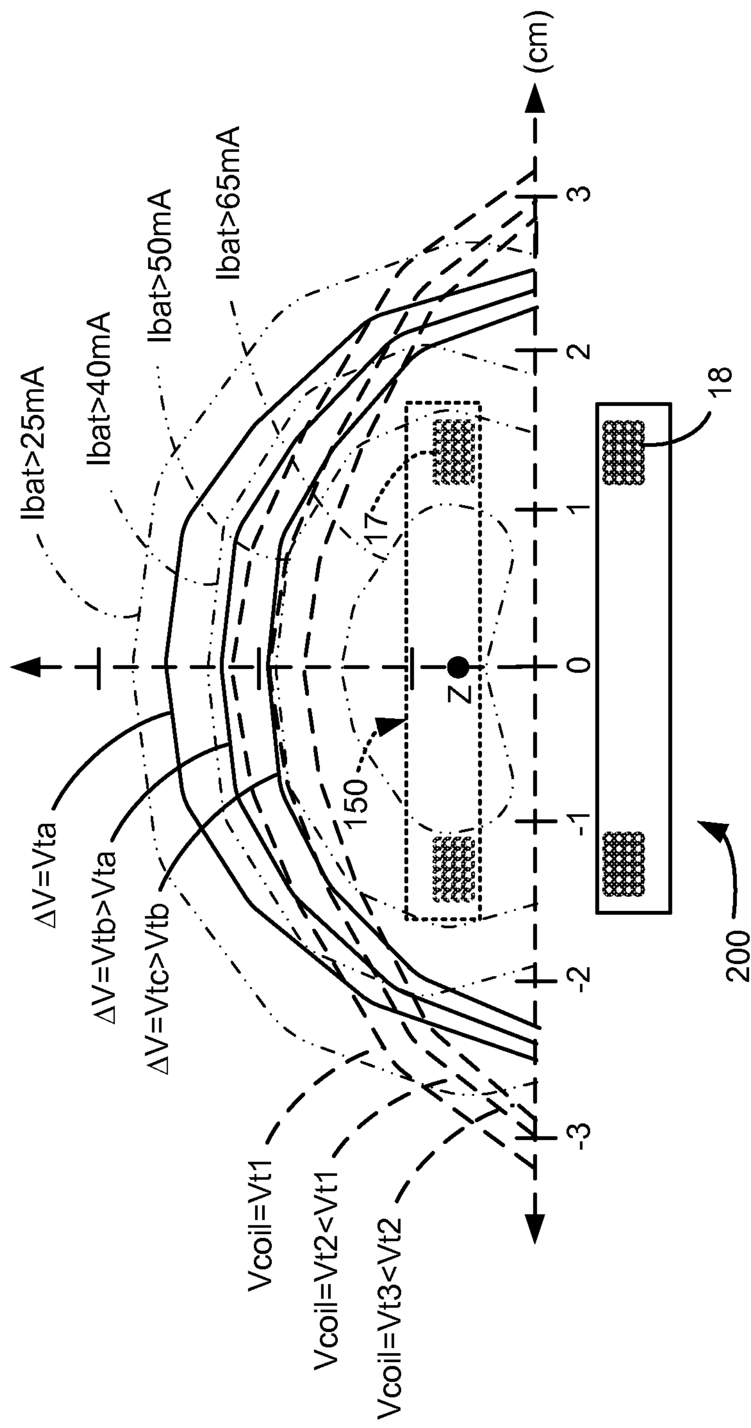
FIG. 6 shows test data indicative of how ΔV (and Vcoil) varies as a function of external charger position relative to the IPG.

The inventors have noticed that the magnitude of ΔV is indicative of the coupling between the coil 17 in the external charger and charging coil 18 in the IPG 200, with ΔV increasing as coupling improves, and decreasing as coupling worsens. This is shown in FIG. 6, which illustrates bench test data showing various constant curves for ΔV. (In reality, these curves are generally hemispherical in three dimensions). In this example, it is assumed that the IPG 200 is implanted at a depth of 0.5 cm beneath a patient's tissue 25, and is implanted perfectly flat. Also shown are potential positions for the external charger 150 (in dotted lines) relative to the IPG 200. A point Z marks the center of the coil 17 in the external charger, and is used generally to indicate the external charger 150's position relative to the IPG 200.

Also shown in FIG. 6 are various regions denoting the charging current received by the IPG's battery 26, Ibat. Each region reflects the resulting Ibat when the external charger 150 is moved so that point Z is located within the region. As would be expected, this empirical data shows that Ibat is highest when point Z (i.e., the external charger 150) is close and centered relative to the IPG 200, as can be seen in the inner most region where Ibat>65 mA. As point Z becomes more distant, or laterally shifts, coupling worsens, and Ibat begins to drop. Even though an IPG 200 is usually implanted at a set depth in the patient's tissue 25 (here, 0.5 cm), and even though the external charger 150 is usually in contact with that tissue, it is useful to consider in FIG. 6 the battery charging current regions at other depths to understand charging performance when that depth varies—i.e., if the implant depth varies or if the distance between the charger and the tissue varies.

Returning to FIG. 5, the coupling detector 160 provides the magnitude of ΔV to the control circuitry 144 in the external charger 150, which in turn controls the charging circuitry 122 to adjust the charging current (Icharge) provided through coil 17. Such control can be affected through proper programming of the control circuitry 144. For example, the control circuitry can contain a table associating ΔV values with desired magnitudes for Icharge. Icharge as determined from the table can be indicated to the charging circuitry along control bus 105. The specifics of the relationship between ΔV and Icharge can be determined experimentally, or through simulations or calculations as one skilled in the art will appreciate. For example, test data such as that shown in FIG. 6 can be useful in this regard. Additionally, such a table can be tailored for individual patients during a fitting procedure, in which can the table would be programmable after manufacture of the external charger 150. Such individualistic tailoring is beneficial, given the particulars of each patient's IPG 200. For example, it cannot be assumed in an actual patient that the patient's IPG 200 has been implanted perfectly flat at a depth of 0.5 cm, as was assumed in FIG. 6. In patients having very deep implants, the ΔV values stored in the table and corresponding to a particular Icharge may need to be relatively small.

If ΔV is relatively small (for a given patient), indicating that coupling is poor and thus that it would take a relatively long time for the battery 26 in the IPG 200 to charge, Icharge is increased. Icharge is an AC varying signal, and so that signal's magnitude is defined in DC terms in any conventional manner, such as by its peak current, its peak-to-peak current, its rms value, etc. Increasing Icharge results is a larger magnetic charging field that will charge the IPG's battery 26 more quickly to compensate for the poor coupling.

By contrast, if ΔV is relatively large, indicating that coupling is good, Icharge can be decreased if necessary. Decreasing Icharge will charge the IPG's battery 26 more slowly, which is generally not desired in its own right. But decreasing Icharge can also provide other benefits, such as reducing the temperature of the external charger 150. It is well know that inductive charging techniques have the propensity to heat both the external charger and the implant, because the magnetic charging field induces eddy currents in the conductive structures in those components. If left unchecked and if uncontrolled, these components can heat to the point of patient discomfort, or even tissue damage. Therefore, the disclosed system benefits by being able to reduce the magnitude of the magnetic charging field if the coupling is high enough and relatively high fields are not needed. As shown in FIG. 5, a temperature sensor 103 provided in the external charger (e.g., a thermocouple) can provide an indication of external charger temperature, T, to the control circuitry 144, and Icharge can be controlled in accordance with the reported temperature T as well as the magnitude of ΔV reported by the coupling detector 160. For example, if ΔV is relatively high, indicating good coupling, but T is relatively low, the control circuitry 144 can inform the charging circuitry 122 to maintain Icharge at a relatively high level. If however ΔV is relatively high, and T is relatively high, the control circuitry 144 can control the charging circuitry 122 to reduce Icharge to try and alleviate concerns about higher temperatures.

Adjustment of Icharge—and hence the strength of the magnetic charging field—can occur periodically during the provision of the magnetic charging field; for example, the strength of the magnetic field can be adjusted in real time as new values (ΔV1, ΔV2, ΔV3, etc.) are determined by the coupling detector 160. It should be noted that as the strength of the magnetic field is adjusted, ΔV may indicate different amounts by which Icharge should be increased or decreased. As such, the table accessible to the control circuitry 144 may be multi-dimensional, and may further indicate an appropriate Icharge given ΔV and given the current level of Icharge.

The detector circuitry 160 may be implemented in any number of ways as one skilled in the art will realize. It may include for example A/D converter circuitry (not shown) for digitally sampling the Vcoil waveform and for processing the result to arrive at accurate ΔV values. The magnitude of ΔV will vary depending on the application, but in one example may range from 150 mV to over a volt. Detector circuitry 160 may average some number of the incoming ΔV values (ΔV1, ΔV2, ΔV3, etc.) over time to render the external charger 150 less susceptible to "spikes" in the ΔV data. The coupling detector 160 can comprise, or be integrated with, the control circuitry 144, which control circuitry 144 can also perform other control functions in the external charger 150 as one skilled in the art will understand. Moreover, although the coupling detector 160 is shown as separate from the demodulator 123 used to discern LSK data, these two circuits blocks can be integrated, at least in part. For example, both the demodulator 123 and the coupling detector 160 can share front end A/D converter circuitry used to sample the Vcoil waveform.

Figure 7:
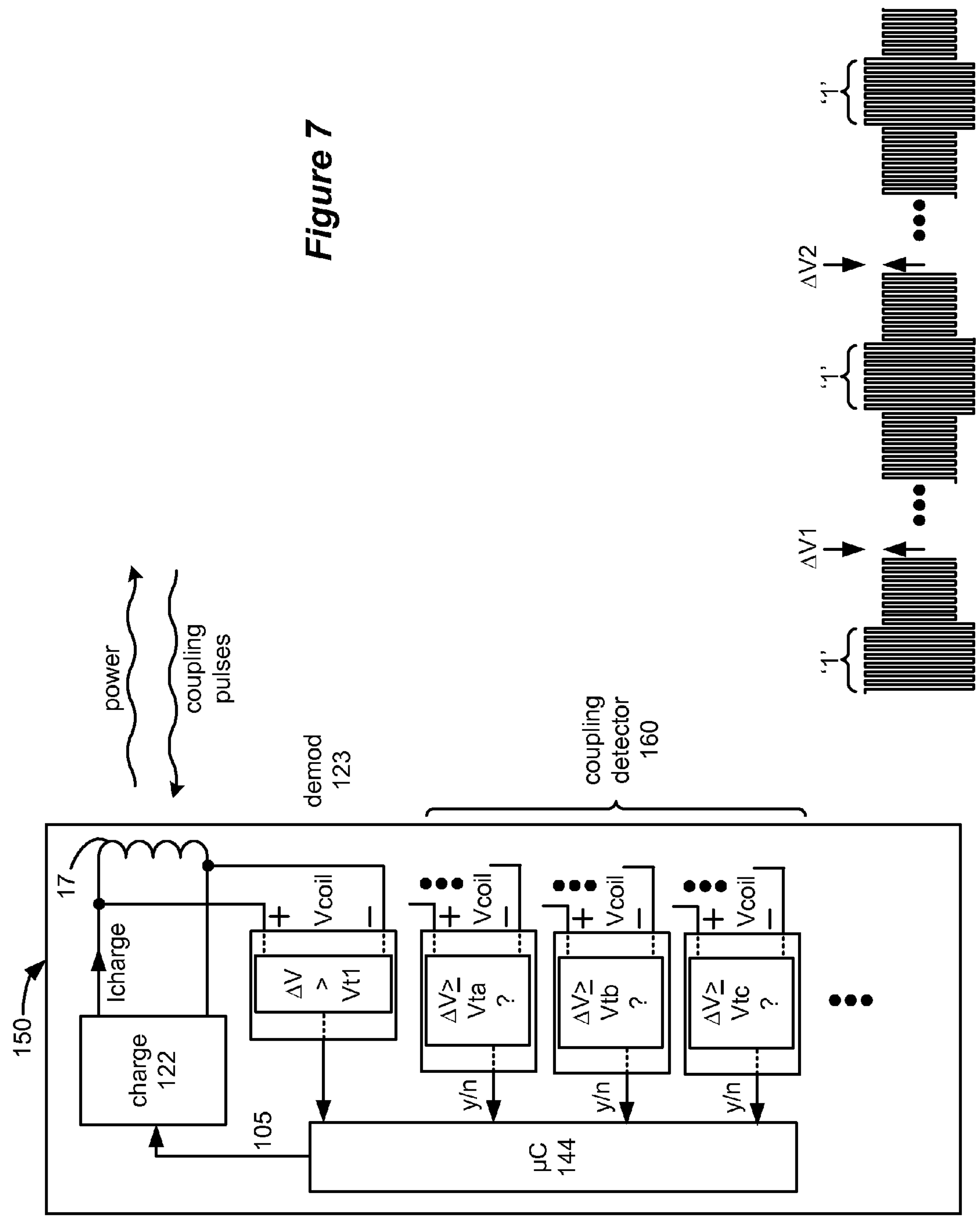
FIG. 7 shows alternative circuitry in the external charger for detecting ΔV using a plurality of comparators.

An alternative structure for the coupling detector 160 is shown in FIG. 7. In this example, the detector 160 is broken up into a plurality of comparators, each for deciding whether ΔV exceeds a particular threshold (Vta, Vtb, Vtc, etc.). Each of the comparators issues a yes/no decision to the control circuitry 144, which can then interpret the results and decide how to control the charging circuitry 122—i.e., how to adjust Icharge flowing through the coil 17. This scheme in effect quantizes the ΔV determination into a series of ranges (ΔV<Vta, Vta<ΔV<Vtb, etc.), which allows Icharge to be similarly quantized. Quantizing the control of the charge current can also be effected in software as well, and so the circuitry of FIG. 5 could also accomplish this.

Figure 8:
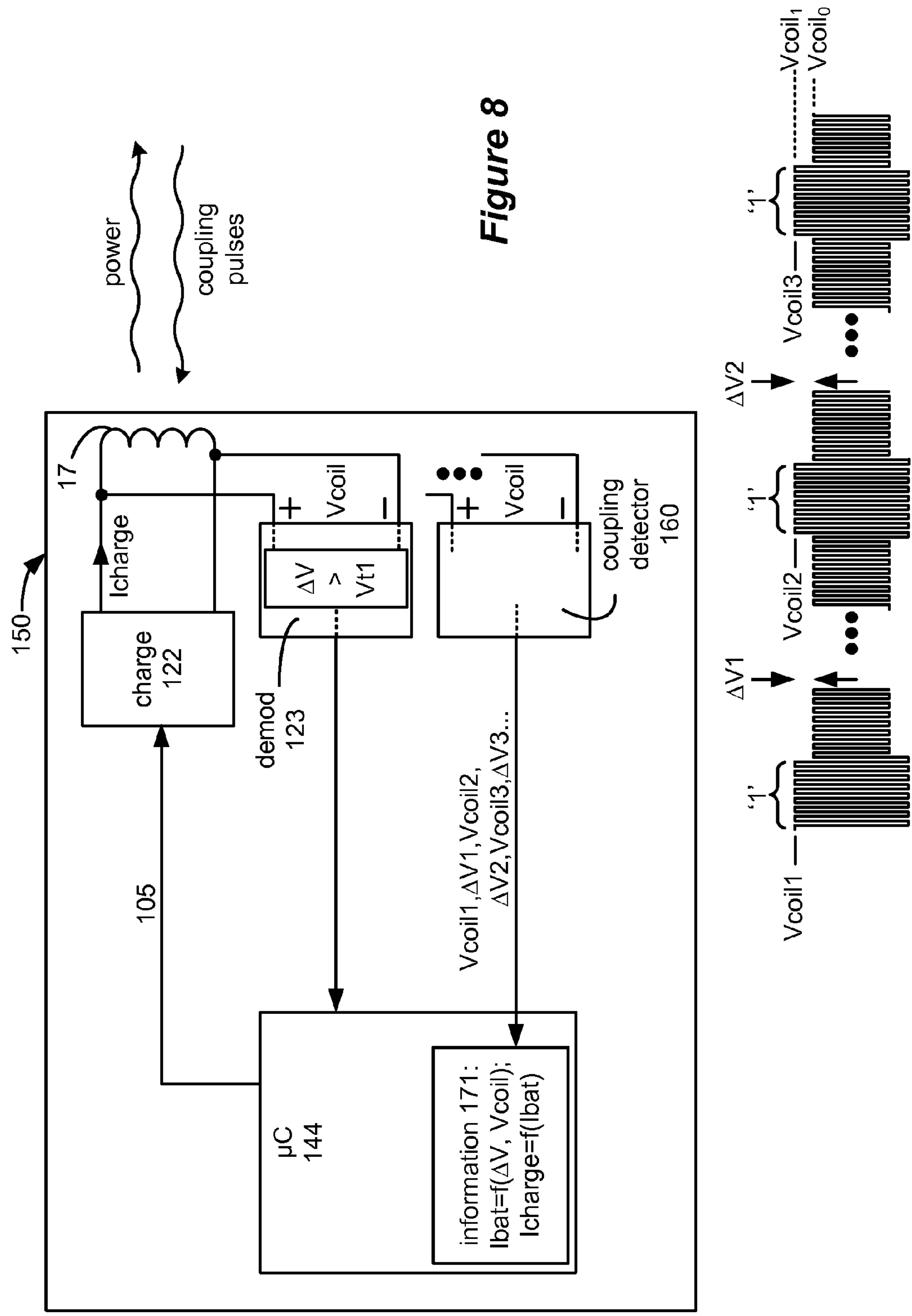
FIG. 8 shows alternative circuitry in the external charger for detecting and using both ΔV and Vcoil to indicate coupling.

FIG. 8 illustrates a modification to the external charger 150/IPG 200 system of FIG. 5. In this case, coupling is determined by considering the magnitudes of both ΔV and Vcoil at the coupling detector 160. The rationale for this modification is illustrated in FIG. 6, which in addition to the constant ΔV curves mentioned previously also shows constant curves for Vcoil. Vcoil is an AC varying signal, and so that signal's magnitude is defined in DC terms in any conventional manner, such as by its peak voltage, its peak-to-peak voltage, its rms value, etc. Note in FIG. 6 that while ΔV generally increases as coupling with the IPG 200 improves, Vcoil generally decreases as coupling with the IPG improves.

Knowledge of the shape of these curves can be used to even better understand the coupling between the external charger 150 and the IPG 200, and thus to better control Icharge in a closed loop fashion. Control circuitry 144 is thus programmed with coupling information 171 relating the battery charging current, Ibat, with ΔV and Vcoil values, which information again may be determined using the types of curves in FIG. 6 for example. Information 171 can generally be similar to the programmed table in the control circuitry 144 referred to earlier, but in this case, such information 170 is more sophisticated and multi-variable. When the coupling detector 160 reports both ΔV and Vcoil magnitudes to the control circuitry 144, the information 171 can be queried to determine an assumed value of Ibat that would result in the IPG 200. That value for Ibat, itself indicative of coupling, can then be used to determine an appropriate value for Icharge, which again is reported to the charging circuitry 122 along control bus 105. By considering both ΔV and Vcoil, a more accurate picture of the coupling between the external charger 150 and the IPG 200 emerges, which then allows Icharge to be set with better accuracy.

It does not particularly matter in FIG. 8 if Vcoil is considered during provision of the alignment pulses ($Vcoil_1$) or during periods between pulses ($Vcoil_0$): ΔV is also considered, which relates $Vcoil_0$ and $Vcoil_1$, so either can be used as representative of the magnitude of Vcoil.

To this point in the disclosure, it has been assumed that data-less periodic coupling pulses provide the modulation at the IPG 200 to provide the reflections at the external charger 150, i.e., the reflections from which ΔV (and possibly also Vcoil) can be assessed according to the disclosed closed loop charging techniques. However, ΔV (and Vcoil) can also be gleaned using different constructs. For example, instead of assessing only coupling pulses, the coupling detector 160 could assess reflections arising from the transmission of actual LSK data, i.e., data otherwise intended for decoding at the demodulator 123. This would be a particularly useful alternative in instances where LSK data is sent from the IPG 200 with sufficient regularity to also function as a means of detecting coupling in accordance with the disclosed techniques. Periodic reporting of the battery capacity might be one such instance in which both LSK data and coupling information could be gleaned from the same reflections at the external charger 150. Moreover, even if actual LSK data is not used, constructs other than single periodic coupling pulses could also be used to produce the necessary reflections.

It has also been assumed that the coil 17 in the external charger 150 is differentially connected to the coupling detector 160, with both ends of the coil 17 being received at the coupling detector 160. However, this is not strictly necessary, and instead a single end of the coil 17 can be received at the coupling detector 160.

It has also been assumed that the coil voltage (ΔV and/or Vcoil) is assessed to make the coupling decision, but this is not strictly necessary, and instead other electrical parameters of the coil could also be assessed. For example, in other embodiments, Vcoil produced by the charging circuitry 122 can be fixed, which would cause the charging current, Icharge, through the coil 17 to vary as the impedance of the coil 18 in the IPG 200 is modulated. The technique could therefore be modified to monitor the current through the coil (ΔIcharge and/or Icoil) to make coupling determinations. Moreover, coil electrical parameters (e.g., voltage or current) could also be processed, scaled, regulated, or buffered before being presented to the coupling detector 160. Any of these means of detection comprises "assessment" of the relevant electrical parameter or its change.

It has also been assumed that the magnetic charging field is used to provide power to charge the battery 26 in the IPG 200. However, the IPG 200 need not contain a battery 26, and instead the external charger 150 can be used to provide continuous power to operate the IPG 200.

Finally, the closed loop charging techniques disclosed herein can be used in conjunction with the above-referenced concurrently-filed application, which uses ΔV (and possibly also Vcoil) to determine and indicate alignment between the external charger and the IPG.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for providing power to an implantable medical device from an external charger, comprising:

providing a magnetic field from a second coil in an external charger;

modulating an impedance of a first coil in the implantable medical device while receiving the magnetic field from the second coil;

determining at least a magnitude of a change in an electrical parameter of the second coil in the external charger caused by modulating the impedance of the first coil;

obtaining a value of a charging parameter using the determined magnitude of the change in the electrical parameter via an established relationship between corresponding charging parameter values and magnitudes of change in the electrical parameter; and adjusting a strength of the magnetic field provided by the second coil in accordance with the obtained value of the charging parameter.

2. The method of claim 1, wherein the impedance of the first coil is modulated by shorting the first coil.

3. The method of claim 1, wherein the impedance of the first coil is modulated by opening the first coil.

4. The method of claim 1, wherein the impedance of the first coil is periodically modulated.

5. The method of claim 1, wherein modulating the impedance of the first coil transmits data to the external charger.

6. The method of claim 1, further comprising determining at least a magnitude of the electrical parameter of the second coil in the external charger, wherein the established relationship comprises a relationship between charging parameter values, magnitudes of the electrical parameter, and magnitudes of change in the electrical parameter, and wherein obtaining the value of the charging parameter comprises obtaining the value from the established relationship using the determined magnitude of the electrical parameter and the determined magnitude of the change in the electrical parameter.

7. The method of claim 1, wherein the implantable medical device comprises a battery, and further comprising using the received magnetic field to recharge the battery.

8. The method of claim 1, wherein the relationship is programmed into control circuitry in the external charger.

9. The method of claim 8, wherein the relationship comprises a table.

10. The method of claim 8, wherein the relationship is determined experimentally.

11. The method of claim 8, wherein the relationship is programmed after implantation of the implantable medical device within a patient.

12. The method of claim 1, further comprising:

measuring a temperature of the external charger; and adjusting the strength of the magnetic field provided by the second coil in accordance with the value of the charging parameter and the measured temperature.

13. The method of claim 1, wherein the relationship is dependent upon an existing value of the charging parameter.

* * * * *